(12) United States Patent
Makkapati et al.

(10) Patent No.: US 10,242,278 B2
(45) Date of Patent: Mar. 26, 2019

(54) DEVICE AND METHOD FOR SKIN DETECTION

(71) Applicant: KONINKLIJKE PHILIPS N.V., Eindhoven (NL)

(72) Inventors: Vishnu Makkapati, Ongole (IN); Ihor Kirenko, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 183 days.

(21) Appl. No.: 14/949,921

(22) Filed: Nov. 24, 2015

(65) Prior Publication Data

US 2016/0155006 A1    Jun. 2, 2016

Related U.S. Application Data

(60) Provisional application No. 62/105,558, filed on Jan. 20, 2015.

(30) Foreign Application Priority Data

Dec. 1, 2014  (IN) ............................ 6011/CHE/2014
Jan. 20, 2015  (EP) ..................................... 15151776

(51) Int. Cl.
*G06K 9/00*     (2006.01)
*G06K 9/20*     (2006.01)
(Continued)

(52) U.S. Cl.
CPC .......... *G06K 9/2036* (2013.01); *A61B 5/0077* (2013.01); *A61B 5/14551* (2013.01);
(Continued)

(58) Field of Classification Search
CPC ............. G06K 9/00362; G06K 9/2018; G06K 9/4661; G06K 9/2036
(Continued)

(56) References Cited

U.S. PATENT DOCUMENTS 8,600,133 B2 * 12/2013 Buelow ................. G06T 7/0012
                                                    382/128
2008/0177185 A1 * 7/2008 Nakao ................. G06K 9/00255
                                                    600/476
(Continued)

FOREIGN PATENT DOCUMENTS

EP    2380493    10/2011
EP    2762066    8/2014
(Continued)

OTHER PUBLICATIONS

Verkruysse et al., "Remote plethysmographic imaging using ambient light", Optics Express, 16(26), Dec. 22, 2008, pp. 21434-21445.
(Continued)

*Primary Examiner* — Van D Huynh

(57) ABSTRACT

A device and a corresponding method for skin detection to enable a reliable, accurate and fast detection are disclosed. The proposed device comprises an illumination unit configured to project a predetermined illumination pattern onto a scene, an imaging unit configured to acquire an image of the scene, and an evaluation unit configured to evaluate the acquired image by analyzing the imaged illumination pattern as reproduced in the image and to detect skin areas within the image and distinguish them from non-skin areas within the image based on said analysis.

20 Claims, 4 Drawing Sheets

(51) Int. Cl.
*A61B 5/00* (2006.01)
*A61B 5/1455* (2006.01)
*A61B 5/024* (2006.01)
*A61B 5/08* (2006.01)
*A61B 5/11* (2006.01)

(52) U.S. Cl.
CPC ....... G06K 9/00362 (2013.01); G06K 9/2018 (2013.01); *A61B 5/02433* (2013.01); *A61B 5/0816* (2013.01); *A61B 5/1114* (2013.01); *A61B 2576/00* (2013.01); *G06K 9/00201* (2013.01)

(58) Field of Classification Search
USPC .......................................... 382/128
See application file for complete search history.

(56) References Cited

U.S. PATENT DOCUMENTS

| | | | |
|---|---|---|---|
| 2011/0213253 A1* | 9/2011 | Kruglick | A61B 5/0064 600/477 |
| 2011/0218428 A1* | 9/2011 | Westmoreland | A61B 6/00 600/425 |
| 2012/0253201 A1 | 10/2012 | Reinhold | |
| 2012/0293700 A1* | 11/2012 | Drouin | G02B 3/005 348/333.1 |
| 2013/0032487 A1 | 12/2013 | Mestha et al. | |
| 2013/0324875 A1 | 12/2013 | Mestha et al. | |
| 2013/0342756 A1* | 12/2013 | Xu | A61B 5/0073 348/370 |
| 2014/0221847 A1* | 8/2014 | Dubielczyk | G06F 19/00 600/479 |
| 2015/0327800 A1* | 11/2015 | Chen | A61B 5/14552 600/480 |

FOREIGN PATENT DOCUMENTS

| | | |
|---|---|---|
| EP | 2779092 | 9/2014 |
| WO | 2013027027 | 2/2013 |
| WO | 2014/014838 | 1/2014 |
| WO | 2014068436 | 5/2014 |
| WO | 2014122126 | 8/2014 |

OTHER PUBLICATIONS

Wieringa, et al., "Contactless Multiple Wavelength Photoplethysmographic Imaging: A First Step Toward "SpO2 Camera" Technology," Ann. Biomed. Eng. 33, 1034-1041 (2005).

Humphreys, et al., "Noncontact simultaneous dual wavelength photoplethysmography: A further step toward noncontact pulse oximetry", Rev. Sci. Instrum. 78, 044304 (2007).

Hong Guo, et al., "Face recognition based on fringe patter analysis", Optical Engineering, vol. 49(3), Mar. 20, 2010.

* cited by examiner

DEVICE AND METHOD FOR SKIN DETECTION

CROSS-REFERENCE TO PRIOR APPLICATIONS

This application claims the benefit of U.S. application Ser. No. 62/105,558 filed Jan. 20, 2015. This application claims the benefit of European Application Serial No. 15151776.0 filed Jan. 20, 2015. This application claims the benefit of Indian Application Serial No. 6011/CHE/2014 filed Dec. 1, 2014. These applications are hereby incorporated by reference herein.

FIELD OF THE INVENTION

The present invention relates to a device and a corresponding method for skin detection.

BACKGROUND OF THE INVENTION

Vital signs of a person, for example the heart rate (HR), the respiration rate (RR) or the arterial blood oxygen saturation (SpO2), serve as indicators of the current health state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Recently, non-contact, remote PPG (rPPG) devices (also called camera rPPG devices) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. This technology particularly has distinct advantages for patients with extreme skin sensitivity requiring vital signs monitoring such as Neonatal Intensive Care Unit (NICU) patients with extremely fragile skin or premature babies.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Wieringa, et al., "Contactless Multiple Wavelength Photoplethysmographic Imaging: A First Step Toward "SpO2 Camera" Technology," Ann Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Apart from the advantage of being fully contactless, cameras (generally called imaging devices) provide 2D information, which allows for a multi-spot and large area measurement, and often contains additional context information. Unlike with contact sensors, which rely on the correct placement on a specific measurement point/area, the regions used to measure pulse signals using rPPG technology are determined from the actual image. Therefore, accurate detection of skin areas, reliable under any illumination conditions becomes a crucial part in the processing chain of a camera-based rPPG device and method.

Currently, there are two main approaches known for reliable detection and tracking of a skin areas.

One approach is based on skin color (RGB-based) detection and segmentation. Methods according to this approach are fast in both detection and tracking of areas with skin color. However, they are not robust to changes of ambient light color, which will change the color of light reflected from a skin area, and are not able to detect skin areas under low illumination conditions or in darkness. Moreover, such methods cannot always differentiate a skin from other objects with the same color.

Another approach is based on extracted PPG signals (PPG-based). Methods according to this approach are more robust in differentiating real skin areas and areas of other object of the same skin color. This approach can be used also to segment the skin areas, which have stronger PPG signal (the most periodic signal). However, the reliability of the approach depends on the robustness of PPG signal extractions, thus it is impacted by motion of a subject and the blood perfusion level. Therefore, if a pulse signal is not periodic or is weak, a camera-based system will have difficulties to detect the segment the skin areas. Moreover, the approach is also computationally expensive.

It should be noted that the detection of skin area is not only of interest in the field of vital signs detection based on the rPPG technology, but also in other technical fields, e.g. in remote gaming applications using camera technology to recognize gestures of the player, face detection, security (robust detection of a person using surveillance cameras and detection of a person wearing a mask), etc.

US 2011/0218428 A1 discloses a structured light illumination (SLI) medical image sensor system that captures one or more images of a skin lesion and generates a 3D surface map of the skin lesion using SLI techniques. A feature detection module processes the 3D surface map to detect certain characteristics of the skin lesion. Feature data of the skin lesion is generated such as size, shape and texture. A feature analysis module processes the feature data of the skin lesion. The feature analysis module compares the skin lesion to prior images and feature data for the skin lesion.

The feature analysis module categorizes the skin lesion based on templates and correlations of types of features.

WO 2014/014838 A2 discloses a system and method for interactive illumination for gesture and/or object recognition.

US 2013/0342756 A1 discloses a system and method for enabling hybrid video capture of a scene being illuminated with structured and unstructured illumination sources.

US 2013/0324875 A1 discloses a system and method for estimating a respiration rate by analyzing distortions in reflections of structured illumination patterns captured in a video containing a view of a subject's thoracic region.

SUMMARY OF THE INVENTION

It is an object of the present invention to provide a device and a corresponding method which allow a reliable, accurate and fast detection of skin.

In a first aspect of the present invention a device for skin detection is presented comprising
   an illumination unit configured to project a predetermined illumination pattern onto a scene,
   an imaging unit configured to acquire an image of the scene, and
   an evaluation unit configured to evaluate the acquired image by analyzing the imaged illumination pattern as reproduced in the image and to detect skin areas within the image and distinguish them from non-skin areas within the image based on said analysis.

In a further aspect of the present invention a corresponding method is presented.

In yet further aspects of the present invention, there are provided a computer program which comprises comprising program code means for controlling a device as disclosed herein to carry out the steps of the method as disclosed herein when said computer program is carried out by the device as well as a non-transitory computer-readable recording medium that stores therein a computer program product, which, when executed by a device as disclosed herein, causes the method disclosed herein to be performed.

Preferred embodiments of the invention are defined in the dependent claims. It shall be understood that the claimed method, computer program and medium have similar and/or identical preferred embodiments as the claimed device and as defined in the dependent claims.

The present invention evaluates the optical properties of skin and its interaction with light at one or more wavelengths. During an interaction of light with skin some amount of the light is reflected directly from the skin surface, while some other amount is diffused and/or absorbed. If a skin area is illuminated by structured light (i.e. an illumination pattern), such as a pattern of dots or sharp lines, the diffusion of the light in skin will blur the edges of the illumination pattern. Further, since skin absorbs a portion of light at certain wavelengths, particularly in the infrared (IR) spectrum, the intensity of reflected light as measured from a skin region will be lower than that of the background. Further, the diffusion factor of light varies depending on the wavelength. For instance, most of the blue light is reflected from a skin surface, while a significant part of infrared light is diffused and/or absorbed in the skin. Further, infrared light is invisible and unobtrusive for the person. These recognitions are exploited according to the present invention by analyzing diffusion and absorption factors of structured light at one or more wavelengths in order to detect skin areas within a scene in which a person or at least a body part of a person is present.

In an embodiment said evaluation unit is configured to compare the imaged illumination pattern with the predetermined illumination pattern as emitted by the illumination unit. Generally, the predetermined illumination pattern, in particular the dimensions and intensities, is known. Since it is also known how the skin changes intensity and causes blur compared to other elements that may be visible in a typical scene, like clothes, fabric (e.g. a linen or blanket) or background (e.g. the wall or furniture), this comparison enables distinguishing skin from other elements.

In another embodiment said evaluation unit is configured to compare separate areas of the imaged illumination pattern to each other. As mentioned above skin causes different changes to the illumination pattern than other elements. Hence comparing different areas, e.g. neighboring pixels or groups of pixels, it can be detected which areas belong to skin areas and which areas do not.

Preferably, said evaluation unit is configured to analyze blur of edges and/or intensities of the imaged illumination pattern. Since the different diffusion and absorption caused by skin compared to other elements mostly effects blur and intensity of the illumination pattern, these features are advantageous for detecting if there is a skin area or not. Hence, blur and/or changes of intensity that are typical for skin may be search to detect skin area.

In this context, it is further preferred that said evaluation unit is configured to compare the amount of edge blur and/or intensities of separate areas, in particular of adjacent pixels and or pixel areas, of the imaged illumination pattern to respective thresholds. This provides for a quite accurate and reliable detection.

The illumination unit may be configured to project said illumination pattern at a single wavelength or a single wavelength range or to project said illumination pattern at two wavelengths or two wavelength ranges. It is further advantageous that said illumination pattern is projected at one or more wavelengths in the infrared spectrum since skin absorbs and/or diffuses infrared radiation more than radiation in the visible spectrum, which does not penetrate very deeply into skin.

Generally, the present invention works with an illumination pattern that is projected at one wavelength. The use of two wavelengths will make the detection more robust to ambient illumination. As explained above, according to the present invention a skin area is detected by detecting a unique "signature", i.e. representing the influence of the skin area on the illumination pattern as detectable in the imaged illumination pattern, such as light diffusion and/or absorption, at a certain wavelength. Theoretically it might happen that other materials would have the same diffusion factor of a specific wavelength as skin. Therefore, adding the one (or more) extra wavelength(s) further strengthens the "signature" (i.e. makes them more unique for skin) and therefore improves the specificity of skin detection because there is a lower probability that there is another material having the same influence on the illumination pattern than skin at those two (or more) wavelengths.

Preferably, in this context said evaluation unit is configured to analyze the differences in edge blur and/or intensities within the image between the two wavelengths or wavelength range and/or to compare the differences in edge blur and/or intensities of separate areas, in particular of adjacent pixels and or pixel areas, of the imaged illumination pattern to respective thresholds. This further improves the detection of skin and makes it more robust against ambient illumination.

In another embodiment said evaluation unit is configured to set and/or adapt said thresholds based on the distance between the illumination unit and the scene and/or the wattage of the illumination unit. For example, if the distance is small and the wattage is high, the thresholds used will be set to higher values and vice versa. This further improves the detection of skin.

In addition to the detection of skin areas the present invention may further be used to obtain information on the size, shape and/or position of skin areas. This is possible with an embodiment in which said evaluation unit is configured to analyze the deformation of the imaged illumination pattern compared to the projected illumination pattern.

The invention is preferably used in the context of vital signs acquisition by use of the rPPG technology. For this purpose said imaging unit is preferably configured to acquire a sequence of images of the scene over time, and said device further comprises a vital signs detector configured to detect vital signs of a subject within the scene based on image information from detected skin areas within said sequence of images. Thus, the proposed detection of skin areas may be once or continuously used to detect and/or track skin areas during the acquisition of vital signs.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
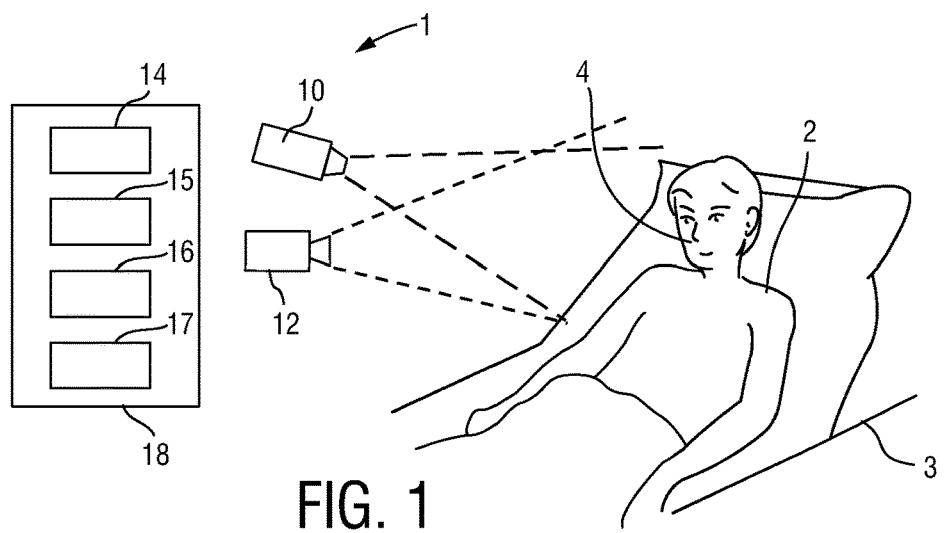
FIG. 1 shows a schematic diagram of a first embodiment of a device according to the present invention.

FIG. 1 shows a schematic diagram of a first embodiment of a device 1 for skin detection according to the present invention. The device 1 comprises an illumination unit 10 for projecting a predetermined illumination pattern onto a scene. The scene includes, in this example, a patient 2 lying in a bed 3, e.g. in a hospital room or other healthcare facility, but may also be the environment of a neonate or premature infant, e.g. lying in an incubator/warmer, or a person at home or in a different environment. The illumination unit 10 may be a special lamp or projector which is configured to generate and emit a predetermined structured light pattern, e.g. a grid or array of lines, crosses, dots or other predefined elements, which preferably have sharp edges.

Further, the device 1 comprises an imaging unit 12 for acquiring an image of the scene. The imaging unit 12 is particularly a camera (also referred to as detection unit or as camera-based or remote PPG sensor), which is configured to obtain images of the scene, preferably including skin areas 4 of the patient 2. In an application of the device for obtaining vital signs of the patient 2, the skin area 4 is preferably an area of the face, such as the cheeks or the forehead, but may also be another area of the body, such as the hands or the arms.

The image frames captured by the camera may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the person. Thereby, an image pixel may correspond to one photosensitive element of a photo-detector and its (analog or digital) output or may be determined based on a combination (e.g. through binning) of a plurality of the photosensitive elements.

The device further comprises an evaluation unit 14 for evaluating the acquired image by analyzing the imaged illumination pattern as reproduced in the image and for detecting skin areas within the image based on said analysis. The device 1 may further comprise a controller 15 for controlling the other elements of the device 1 and user interface, such as a keyboard and/or a display 16 for entering commands for controlling the device 1 and/or outputting generated information, such as obtained vital signs. Still further, the device 1 preferably comprises a vital signs detector 17 for detecting vital signs of a person 2 within the scene based on image information from detected skin areas within a sequence of images acquired by the imaging unit 12.

The units 14 to 17 may be configured as dedicated hardware elements, but may also be configured as processor or computer 18, which is programmed accordingly. The device 1 may be configured as integrated device including all its elements and units, e.g. in a common housing (e.g. in the housing of the imaging unit 10) or as distributed device, as shown in FIG. 1, in which the elements and units may be distributed, i.e. implemented as separate elements and units arranged at different positions.

Figure 2:
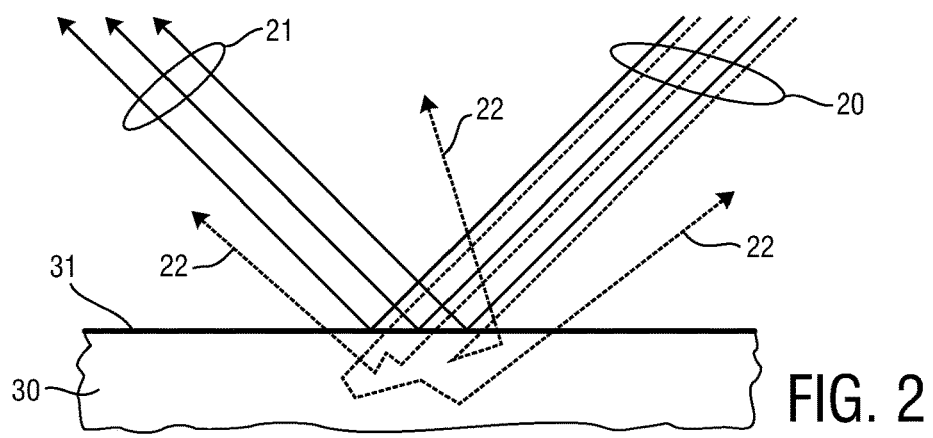
FIG. 2 shows a diagram illustrating the diffusion and reflection of light during interaction with skin.
Figure 3:
FIG. 3 shows a diagram illustrating an example of an illumination pattern that may be used according to the present invention.

The present invention is based on the optical properties of skin and its interaction with light at one or more wavelengths, preferably in the infrared spectrum. FIG. 2 shows a diagram illustrating the diffusion and reflection of light 20 during interaction with skin 30. During an interaction of light with skin, some amount of the light 21 is reflected directly from the skin surface 31, and some other amount of light 22 is diffused and/or absorbed. If a skin area is illuminated by structured light, e.g. lines having sharp edges as shown in FIG. 3 as an example of a structured illumination pattern, the diffusion of the light in skin will blur the edges of the structured lines. Further, since skin absorbs a portion of light at certain wavelengths in the IR spectrum, the intensity of IR reflection as measured from the skin region will be lower than that of the background.

Further, as explained above the diffusion factor of light varies depending on the wavelength, i.e. most of the blue light is reflected from a skin surface, while a significant part of IR light is diffused and/or absorbed in the skin. Hence, by analyzing diffusion and absorption factors of structured light at one or more wavelengths, preferably in the IR spectrum, allows accurate, reliable and fast detection of skin areas in a scene as reflected in (one or more) image(s).

The invention is preferably applied in the field of rPPG for the acquisition of vital signs of the person. Thus, the images obtained by the imaging unit 12 are not only used for detecting skin areas as explained above, but from detected (and preferably tracked, also by use of the present invention) skin areas PPG signals are derived, which are used for deriving vital signs of the person, such as heartbeat, SpO2, etc. The imaging unit 12 is at least sensitive at the wavelength(s) or wavelength ranges, in which the illumination pattern is projected onto the person, but may be sensitive for other wavelengths as well, in particular if required for obtaining the desired vital signs. Further, the evaluation unit 14 may be configured to select the appropriate wavelengths from the images to detect skin area(s) and, if desired, to derive vital sign(s) from the detected skin area(s) using the rPPG technology and/or by analyzing the periodic motion to obtain breathing information such as the breathing rate.

Due to different penetration depth of IR light at various wavelengths, the diffusion factor for those wavelengths will be different. The exact diffusion factor for each of the wavelengths in tissue is defined by the optical properties of that tissue. By analyzing the diffusion and absorption factors of the wavelengths, the optical properties specific for a skin tissue can be defined. In this way, skin tissue can be differentiated from other tissues.

Figure 4:
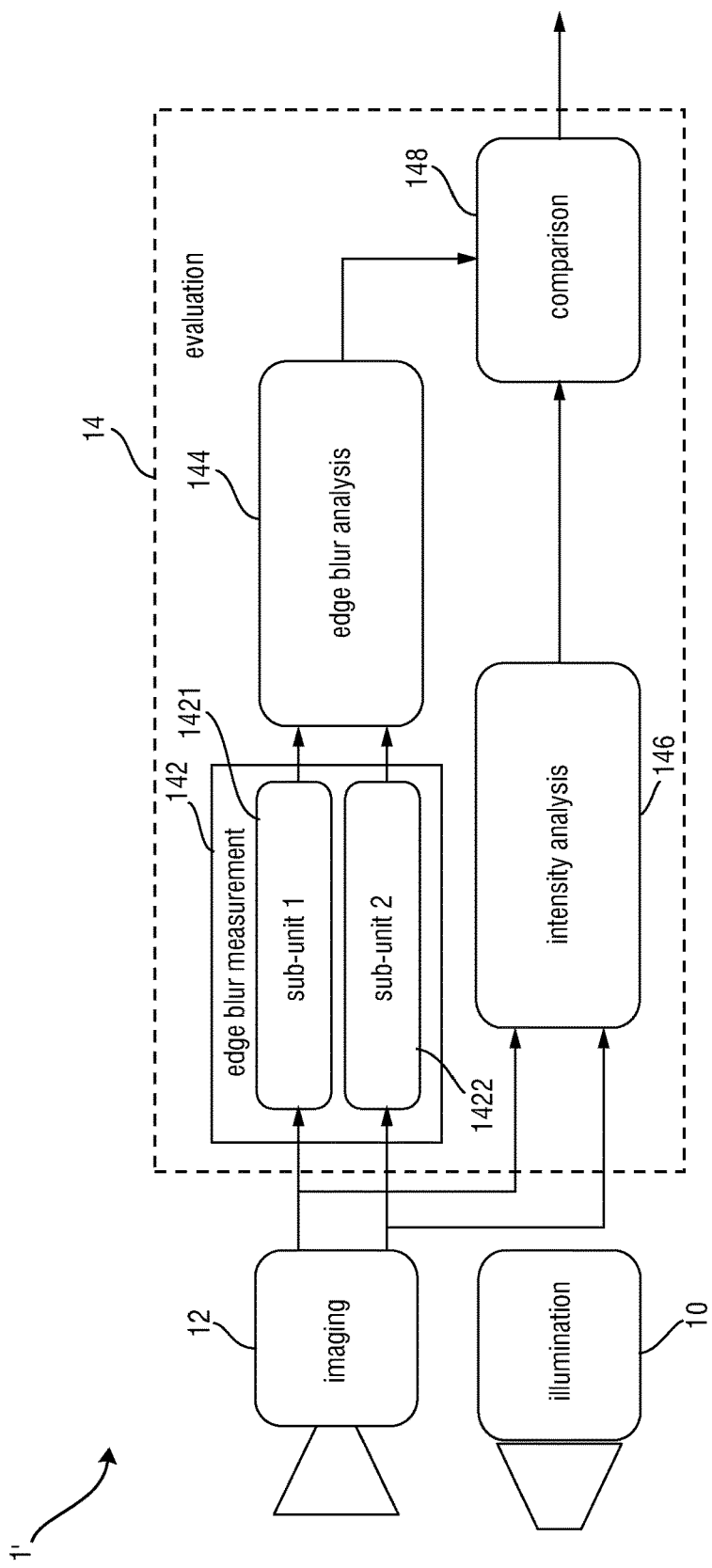
FIG. 4 shows a schematic diagram of a second embodiment of a device according to the present invention.
Figure 5A:
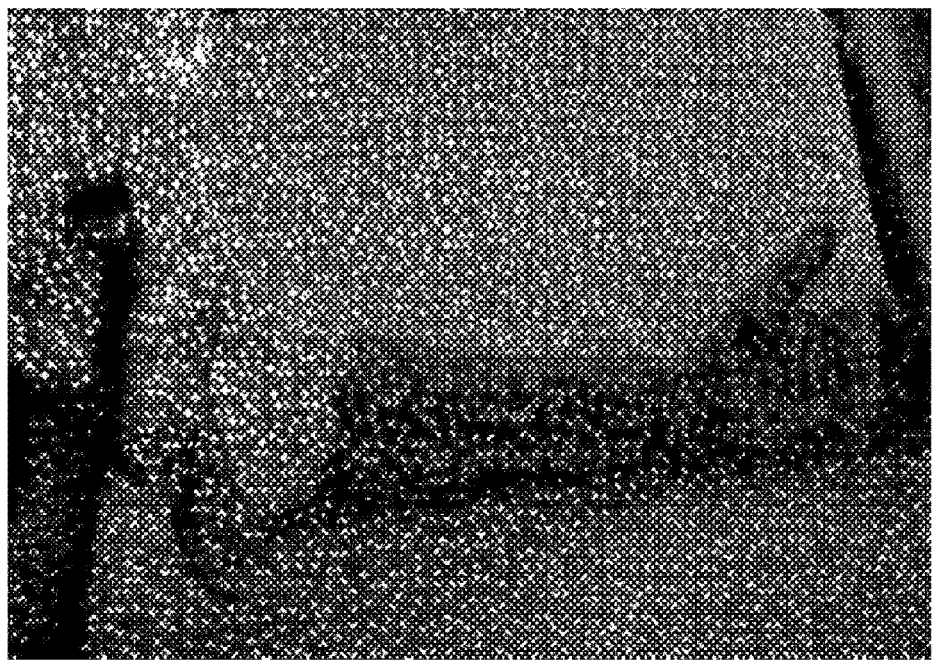
FIG. 5A shows a diagram illustrating an example of an imaged illumination pattern as imaged from a scene including a skin area.

FIG. 4 shows a schematic diagram of a second embodiment of a device 1' according to the present invention. An exemplary dot pattern that may be used as illumination pattern is depicted in FIG. 4A as projected on the person's hand. The IR dot pattern shown in FIG. 5A projected is of an exemplary wavelength of 830 nm (near IR) where human skin has a significant absorption coefficient. It can be noticed from FIG. 5A that the intensity of the dots present on human skin is less than that of speckles present on other objects, which have lower absorption coefficients (e.g. clothes). This fact is used to segment the human skin by thresholding the intensity values. To compensate a possible impact of ambient light at the same wavelength, the intensity of the dots versus the intensity of adjacent pixels (not illuminated by structured light) is analyzed.

To further improve the robustness (and specificity) of skin detection using this approach, an illumination pattern projected at at least two IR wavelengths is used in this embodiment, preferably in the near IR spectrum. Skin areas can be segmented by comparing the differences in intensities values of adjacent dots of different (near IR) wavelengths. For this purpose the image acquired by the imaging unit 12 is provided to an edge blur measurement unit 142 of the evaluation unit 14 (depicted are two sub-units 1421 and 1422 of edge blur measurement unit 142 for the two wavelengths since the edge blur in the provided image is evaluated separately at the two wavelengths) for detecting edge blur of the illumination pattern caused by the skin or other elements in the scene. In an edge blur analysis unit 144 the differences in edge blur at the two wavelengths as detected by the sub-units 1421 and 1422 are analyzed. Further, the image acquired by the imaging unit 12 is provided to an intensity analysis unit 146 of the evaluation unit 14 for analyzing the differences of the intensities of the illumination pattern at the two wavelengths.

A comparison unit 148 is provided for comparing the edge blur and intensity differences as detected by the analysis units 144 and 146. Based on this comparison it is decided if and which areas of the image are skin areas and which areas are no skin areas.

In the above described way as used in the embodiment of the device 1' the method is robust to ambient IR illumination, which might change the intensity values of IR dots, but would not change the difference between the intensity values of dots of different IR wavelengths since ambient IR light will make an equal contribution to all dots from both IR wavelengths.

Figure 5B:
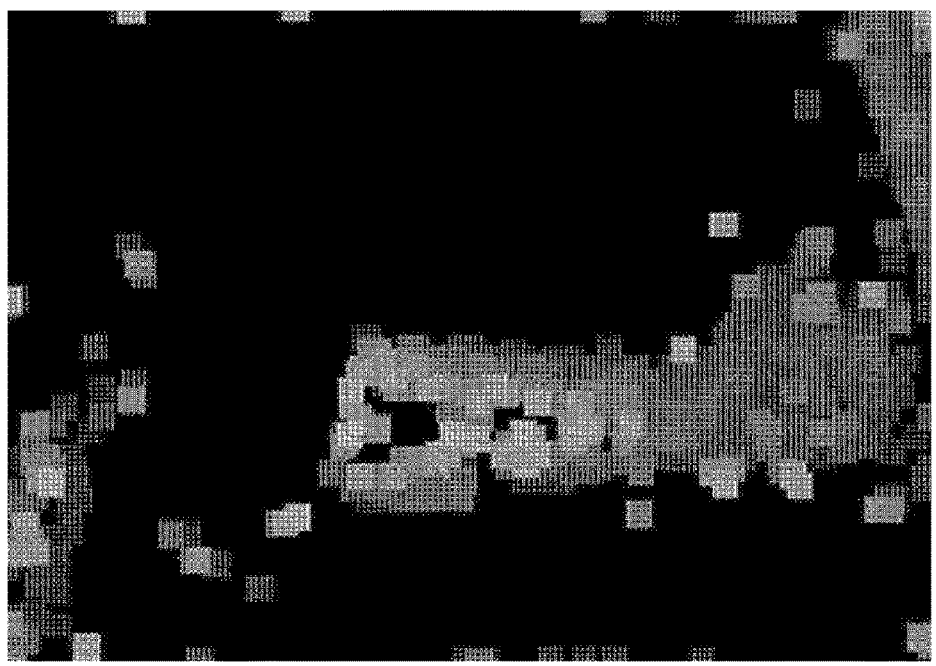
FIG. 5B shows a diagram illustrating an example of a result of the proposed skin detection.

Preferably, the illumination unit 10 and the imaging unit 12 are arranged within a range of fixed distance from the person being monitored. Hence, lower and upper bounds suited to segment illumination pattern (e.g. the dots) on the skin can be selected based on the distance and the wattage of light sources (e.g. IR LEDs) of the illumination unit 10. Further, the dimensions of the illumination pattern, e.g. the radius of the circular dots, is generally known a priori and can be used to estimate the blur caused by diffusion of IR light in the skin. FIG. 5B shows the result of skin segmentation for the image shown in FIG. 5A.

In another embodiment of the present invention, the proposed analysis of the structured light diffusion can be combined with a method for skin detection, e.g. the analysis of chrominance or temporal pulsatility of the structured light reflected from the skin area as generally known. In yet another embodiment of the present invention, structured illumination pattern comprising more than two wavelengths in the visible and preferably the IR spectrum is used to improve the specificity of skin area detection. Still further, in an embodiment of the present invention, the deformation of the structured illumination pattern is used to analyze the shape of the area, thus improving the specificity of the skin detection method. Even further, in another embodiment of the present invention, the proposed device can be integrated with a 3D camera system based on the illumination pattern to derive e.g. a depth map by analyzing the changes of the spatial structure of dots, or the present invention can be used in existing devices, which acquire a depth map, to additionally detect skin areas.

Figure 6:
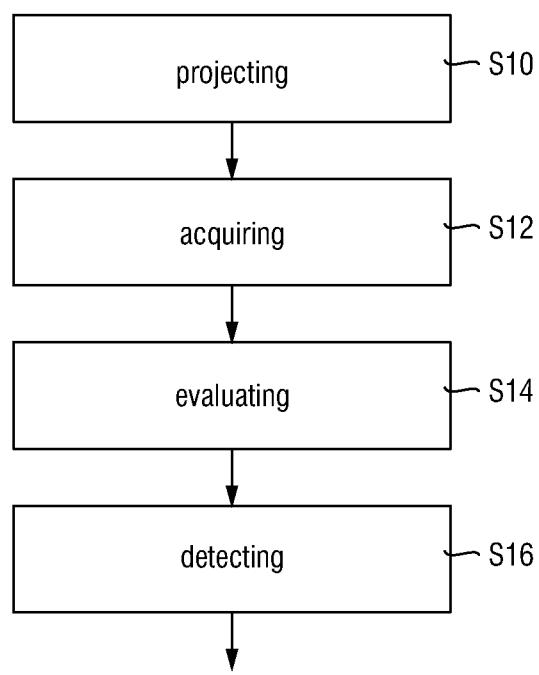
FIG. 6 shows a flow chart of an embodiment of a method according to the present invention.

FIG. 6 shows a flow chart of an embodiment of a method for skin detection according to the present invention. In a first step S10 a predetermined illumination pattern is projected onto a scene. In a second step S12 an image of the scene acquired (once or multiple times or regularly or continuously). In a third step S14 the acquired image is evaluated by analyzing the imaged illumination pattern as reproduced in the image. Finally, in a fourth step S16 skin areas are detected within the image based on said analysis. The method may comprise further steps and may be modified as explained above for the various embodiments of the device and as disclosed herein.

The proposed device and method can be used for continuous unobtrusive monitoring of PPG related vital signs (e.g. heartbeat, SpO2, respiration), and can be used in NICU, Operation Room, or General Ward. The proposed device and method can be also used for personal health monitoring. Generally, the present invention can be used in all application where skin needs to be detected in an image of a scene and needs particularly be distinguished from non-skin.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. A device for skin detection comprising:
an illumination unit configured to project a predetermined illumination pattern onto a scene;
an imaging unit configured to acquire an image of the scene;
an evaluation unit configured to evaluate the acquired image by analyzing blur of edges of the imaged illumination pattern as reproduced in the image and detecting skin areas within the image based on the analysis of the blur of the edges and distinguishing the skin areas from non-skin areas within the image based on said analysis of the blur of the edges;
a vital signs detector configured to detect vital signs of a subject within the scene based on image information from the detected skin areas within the acquired image; and
a display device configured to display the detected vital signs.

2. The device as claimed in claim 1,
wherein said evaluation unit is configured to compare the imaged illumination pattern with the predetermined illumination pattern as emitted by the illumination unit.

3. The device as claimed in claim 1,
wherein said evaluation unit is configured to compare separate areas of the imaged illumination pattern to each other.

4. The device as claimed in claim 1,
wherein said evaluation unit is configured to compare the amount of edge blur of adjacent pixels and or pixel areas, of the imaged illumination pattern to respective thresholds.

5. The device as claimed in claim 4,
wherein said evaluation unit is configured to set and/or adapt said thresholds based on the distance between the illumination unit and the scene and/or the wattage of the illumination unit.

6. The device as claimed in claim 1,
wherein said illumination unit is configured to project said illumination pattern at a single wavelength or a single wavelength range.

7. The device as claimed in claim 1,
wherein said illumination unit is configured to project said illumination pattern at two wavelengths or two wavelength ranges.

8. The device as claimed in claim 7,
wherein said evaluation unit is configured to analyze the differences in edge blur within the image between the two wavelengths or wavelength ranges.

9. The device as claimed in claim 8,
wherein said evaluation unit is configured to compare the differences in edge blur of adjacent pixels and or pixel areas, of the imaged illumination pattern to respective thresholds.

10. The device as claimed in claim 1,
wherein said illumination unit is configured to project said illumination pattern at one or more wavelengths in the infrared spectrum.

11. The device as claimed in claim 1,
wherein said evaluation unit is configured to analyze the deformation of the imaged illumination pattern compared to the projected illumination pattern to obtain information on the size, shape and/or position of skin areas.

12. The device as claimed in claim 1,
wherein said imaging unit is configured to acquire a sequence of images of the scene over time, and
wherein the vital signs detector is configured to detect vital signs of a subject within the scene based on image information from the detected skin areas within said sequence of images.

13. A method for skin detection comprising:
projecting a predetermined illumination pattern comprising a grid or array of lines, crosses, or dots onto a scene,
acquiring an image of the scene,
evaluating the acquired image by analyzing the imaged illumination pattern as reproduced the image by analyzing blur of edges of the imaged illumination pattern as reproduced in the image;
detecting skin areas within the image and distinguishing them from non-skin areas within the image based on said analysis;
detecting vital signs of a subject within the scene based on image information from the detected skin areas; and
displaying the detected vital signs on a display device.

14. A non-transitory computer readable non-transitory medium having instructions stored thereon which, when carried out on a computer, cause a device to perform the steps of the method as claimed in claim 13.

15. A device for skin detection, the device comprising:
a light source configured to project a predetermined illumination pattern onto a scene;
a camera configured to acquire an image of the scene;
at least one computer processor programmed to:
evaluate the acquired image by analyzing blur of edges of the imaged illumination pattern as reproduced in the image;
detect skin areas within the image based on the analysis;
distinguish the detected skin areas from non-skin areas within the image based on the analysis; and
detect vital signs of a subject within the scene based on image information from the detected skin areas within the acquired image.

16. The device as claimed in claim 15, wherein the light source projects the predetermined illumination patterns comprising a wavelength in the infrared and the at least one computer processor is programmed to:
detect skin areas based at least one higher edge blur of the imaged illumination pattern in skin areas compared with non-skin areas.

17. The device as claimed in claim 15, wherein the light source projects the predetermined illumination pattern comprising a wavelength in the infrared and the at least one computer processor is programmed to:
detect skin areas based on lower intensities of the imaged illumination pattern in skin areas compared with non-skin areas.

18. The device as claimed in claim 15, wherein the at least one computer processor is further programmed to:
set and/or adapt said thresholds based on the distance between the light source and the scene and/or the wattage of the light source.

19. The device as claimed in claim 15, wherein the at least one computer processor is further programmed to:
analyze the deformation of the imaged illumination pattern compared to the projected illumination pattern to obtain information on the size, shape and/or position of skin areas.

20. The device as claimed in claim 15,
wherein the camera is configured to acquire a sequence of images of the scene over time, and
wherein the at least one computer processor is further programmed to detect vital signs of a subject within the scene based on image information from detected skin areas within said sequence of images.

* * * * *